United States Patent
Bolt et al.

(10) Patent No.: US 6,706,265 B1
(45) Date of Patent: *Mar. 16, 2004

(54) HUMANIZED ANTI-CD3 SPECIFIC ANTIBODIES

(75) Inventors: Sarah L. Bolt, Cambridge (GB); Michael R. Clark, Cambridge (GB); Scott D. Gorman, Oxfordshire (GB); Edward G. Routledge, Newcastle (GB); Herman Waldmann, Oxfordshire (GB)

(73) Assignee: BTG International Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 08/478,684

(22) Filed: Jun. 7, 1995

Related U.S. Application Data

(63) Continuation of application No. 07/988,925, filed as application No. PCT/GB92/01933 on Oct. 21, 1992, now Pat. No. 5,585,097.

(30) Foreign Application Priority Data

Mar. 24, 1992 (GB) .............................................. 9206422

(51) Int. Cl.[7] ...................... A61K 39/395; C07K 16/00; C12P 21/08
(52) U.S. Cl. ................................ 424/133.1; 424/154.1; 530/387.1; 530/388.2; 530/387.3; 530/388.75
(58) Field of Search .......................... 530/387.3, 388.75, 530/387.1, 388.2; 424/154.1, 133.1

(56) References Cited

U.S. PATENT DOCUMENTS

| | | |
|---|---|---|
| 5,225,539 A | 7/1993 | Winter |
| 5,968,509 A * | 10/1999 | Gorman et al. |

FOREIGN PATENT DOCUMENTS

| | | |
|---|---|---|
| EP | 0 239 400 | 9/1987 |
| EP | 0 336 379 | 10/1989 |
| EP | 0 359 096 | 3/1990 |
| GB | 2 216 126 B | 10/1989 |
| WO | WO 88/07089 | 9/1988 |
| WO | WO 89/07452 | 8/1989 |
| WO | WO 90/10700 | 9/1990 |
| WO | WO 91/09966 | 7/1991 |
| WO | WO 91/09968 | 7/1991 |
| WO | WO 91/10752 | 7/1991 |
| WO | WO 92/09967 | 6/1992 |
| WO | WO 92/22653 | 12/1992 |

OTHER PUBLICATIONS

Osband, Immunol. Today, 1990, 11:193.*
Ngo et al. The Protein Folding Problem and Tertiary Structure Determination. K. Merz and S. LeGrand, Eds., Birkhauser Boston, 1994, pp. 492–495.*
Kabat and Wu, J. Immunol., 1991, 147:1709.
Clement, L.T. et al "Analysis of the monocyte . . . " The Jour of Immunol, vol 135, No. 1 (Jul. 1985), pp. 165–171.
Alegre, M.L. et al "Effect of a single amino acid . . . " The Jour of Immunol, vol 148 No 11 (Jun. 1, 1992), pp. 3461–3468.
Gorman, S.D. et al "Reshaping a therapeutic . . . " Proc Natl Aca Sci, USA, vol 88 (May 1991), pp. 4181–4185.
Routledge, E.G. et al "A humanized monovalent CD3 . . . " Euro Jour of Immunol, (Nov. 1991), pp. 2649–2898.
Gorman, S.D. et al "Humanisation of monoclonal . . . " seminars in Immunology, vol 2 (1990), pp. 457–466.
Tao, Mi–Hua, et al "Studies of aglycosylated chimeric . . . " Jour of Immunol, vol 143 No 8 (Oct. 15, 1989), pp. 2595–2601.
Clark, M. et al "The improved lytic function and in vivo . . . " Euro Jour Immunol, vol 19 (1989), pp. 381–388.
Moore, G.P. "Genetically Engineered Antibodies" Clin Chem (1989), 35/9 (1989), pp. 1849–1853.

* cited by examiner

Primary Examiner—Christina Chan
Assistant Examiner—Marianne DiBrino
(74) Attorney, Agent, or Firm—Nixon & Vanderhye P.C.

(57) ABSTRACT

Novel aglycosylated antibodies having a binding affinity for the CD3 antigen complex are of value for use in therapy, particularly in immunosuppression.

20 Claims, 7 Drawing Sheets

HUMANIZED ANTI-CD3 SPECIFIC ANTIBODIES

This is a Rule 60 continuation of application Ser. No. 07/988,926 now U.S. Pat. No. 5,585,097 filed Nov. 8, 1993, which is a 371 of PCT/GB92/01933, filed Oct. 21, 1992.

BACKGROUND OF THE INVENTION

This invention relates to novel antibodies, in particular to antibodies directed against the CD3 antigen complex.

Antibodies, or immunoglobulins, comprise two heavy chains linked together by disulphide bonds and two light chains, each light chain being linked to a respective heavy chain by disulphide bonds in a "Y" shaped configuration. The two "arms" of the antibody are responsible for antigen binding, and include regions where the polypeptide structure varies, these "arms" being termed Fab' fragments (fragment—antigen—binding) or $F(ab')_2$ which represents two Fab' arms linked together by disulphide bonds. The "tail" or central axis of the antibody contains a fixed or constant sequence of peptides and is termed the Fc fragment (fragment—crystalline). The production of monoclonal antibodies was first disclosed by Kohler and Milstein (Kohler & Milstein, Nature, 256, 495–497 (1975)). Such monoclonal antibodies have found widespread use as diagnostic agents and also in therapy.

Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain (CH1). The constant domains in the light and heavy chains are not involved directly in binding the antibody to antigen. The light chain constant domain and the CH1 domain of the heavy chain account for 50% of each Fab' fragment.

The variable domains of each pair of light and heavy chains form the antigen binding site. The domains on the light and heavy chains have the same general structure and each domain comprises four framework regions, whose sequences are relatively conserved, connected by three complementarity determining regions (CDRs) (Kabat et al, Sequences of Proteins of Immunological Interest, U.S. Department of Health and Human Services (1987)). The four framework regions largely adopt a beta-sheet conformation and the CDRs form loops connecting, and in some cases forming part of, the beta-sheet structure. The CDRs are held in close proximity by the framework regions and, with the CORs from the other domain, contribute to the formation of the antigen binding site.

The human CD3 antigen consists of a minimum of four invariant polypeptide chains, which are non-covalently associated with the T-cell receptors on the surface of T-cells, and is generally now referred to as the CD3 antigen complex. It is intimately involved in the process of T-cell activation in response to antigen recognition by the T-cell receptors.

All CD3 monoclonal antibodies can be used to sensitise T-cells to secondary proliferative stimuli such as IL1 (interleukin 1) and IL2 (interleukin 2). In addition, certain CD3 monoclonal antibodies are themselves mitogenic for T-cells. This property is isotype dependent and results from the interaction of the CD3 antibody Fc domain with Fc receptors on the surface of accessory cells.

Rodent CD3 antibodies have been used to influence immunological status by suppressing, enhancing or re-directing T-cell responses to antigens. They therefore have considerable therapeutic potential in the human for use as an immunosuppressive agent, for example for the treatment of rejection episodes following the transplantation of renal, hepatic and cardiac allografts. However their value is compromised by two main factors. The first is the antiglobulin response evoked due to the xenogeneic nature of the antibody. The second is the "first dose" syndrome experienced by patients following the initial administration of the antibody. The symptoms, which range in severity from fever and chills to pulmonary edema, and which in rare cases can cause death, are caused by the elevated levels of circulating cytokines associated with CD3-antibody induced T-cell activation. This phenomenon requires the cross-linking of the CD3 antigen on the surface of T-cells to accessory cells through Fc receptors; such proliferation does not occur with $F(ab')_2$ fragments of CD3 antibodies.

The first problem can be addressed by re-shaping or "humanising" the variable region genes of antibodies and expressing them in association with relevant human constant domain genes. This reduces the non-human content of the monoclonal antibody to such a low level that an antiglobulin response is unlikely. Such a reshaped antibody with a binding affinity for the CD3 antigen complex is described in UK Patent Application No. 9121126.8 (published as GB 2249310A) and its equivalents (European Patent Application No. 91917169.4, Japanese Patent Application No. 516117/91 and U.S. patent application Ser. No. 07/862,543).

There remains however the problem of the first dose response when these antibodies are used in therapy. Aglycosylation of antibodies has been described to reduce their ability to bind to Fc receptors in vitro in some cases. However, it is not predictable that this will be true of all antibodies, particularly in vivo, and aglycosylation may result in the introduction into the antibody of novel and unpredictable properties including novel Fc binding characteristics causing other undesirable effects. It is also possible that other undesirable properties not associated with Fc binding may be introduced to the antibody.

Moreover, it is of course of vital importance that aglycosylation is not accompanied by the loss of certain desirable features of Fc binding in addition to the loss of the undesirable features such as those attributable to the first dose response.

DESCRIPTION OF THE INVENTION

It has now been found, however, that it is possible to produce aglycosylated CD3 antibodies of the IgG subclass which surprisingly retain their antigen binding specificity and immunosuppressive properties and yet do not induce T cell mitogenesis in vitro and induce a reduced level of cytokine release in vivo, whilst still maintaining some Fc binding ability.

Accordingly, the invention provides an aglycosylated IgG antibody having a binding affinity for the CD3 antigen complex.

The term aglycosylated is employed in its normal usage to indicate that the antibodies according to the invention are not glycosylated. Although the present invention can be applied to antibodies having a binding affinity for a non-human CD3 antigen complex, for example various other mammalian CD3 antigens for veterinary use, the primary value of the invention lies in aglycosylated antibodies having an affinity for the human CD3 antigen complex for use in the human and the following discussion is particularly directed to that context.

Further discussion of CD3 antigens is to be found in the report of the First International Workshop and Conference on Human Leukocyte Differentiation Antigens and description of various glycosylated antibodies directed against the CD3 antigen is also to be found in the reports of this series of Workshops and Conferences, particularly the Third and Fourth, published by Oxford University Press. Specific examples of such antibodies include those described by Van Ller et al., Euro. J. Immunol., 1987, 17, 1599–1604, Alegre et al., J. Immunol., 1991, 140, 1184, and by Smith et al., ibid, 1986, 16, 478, the last publication relating to the IgG1 antibody UCHT1 and variants thereof. However, of particular interest as the basis for aglycosylated antibodies according to the present invention are the CDRs contained in the antibodies OKT3 and YTH 12.5.14.2. The antibody OKT3 is discussed in publications such as Chatenaud et al., Transplantation, 1991, 51, 334 and the New England Journal of Medicine paper, 1985, 313, 339, and also in European Patent No. 0 018 795 and US Pat. No. 4,361,539. The antibody YTH 12.5.14.2 (hereinafter referred to as YTH 12.5) is discussed in publications such as Clark et al., European3J. Immunol., 1989, 19, 381–388 and reshaped YTH 12.5, antibodies are the subject of UK Patent Application No. 9121126.8 and its equivalents, this application describing in detail the CDRs present in this antibody.

Aglycosylated antibodies containing one or more of the CDRs described in the above application are of particular interest. Thus the antibodies of the invention preferably have at least one CDR selected from the amino acid sequences:

(a) Ser-Phe-Pro-Met-Ala (SEQUENCE ID NO. 1), (b) Thr-Ile-Ser-Thr-Ser-Gly-Gly-Arg-Thr-Tyr-Tyr-Arg-Asp-Ser-Val-Lys-Gly (SEQUENCE ID NO. 2), (c) Phe-Arg-Gln-Tyr-Ser-Gly-Gly-Phe-Asp-Tyr (SEQUENCE ID NO. 3), (d) Thr-Leu-Ser-Ser-Gly-Asn-Ile-Glu-Asn-Asn-Tyr-Val-His (SEQUENCE ID NO. 4), (e) Asp-Asp-Asp-Lys-Arg-Pro-Asp (SEQUENCE ID NO. 5), (f) His-Ser-Tyr-Val-Ser-Ser-Phe-Asn-Val (SEQUENCE ID NO. 6), and conservatively modified variants thereof.

The term "conservatively modified variants" is one well known in the art and indicates variants containing changes which are substantially without effect on antibody-antigen affinity.

The CDRs are situated within framework regions of the heavy chain (for (a), (b) and (c)) and light chain (for (d), (e) and (f)) variable domains. The antibody also comprises a constant domain.

In a preferred embodiment the aglycosylated antibody has three CDRs corresponding to the amino acid sequences (a), (b) and (c) above or conservatively modified variants thereof and/or three CDRs corresponding to amino acid sequences (d), (e) and (f) or conservatively modified variants thereof, the heavy chain CDRs (a), (b) and (c) being of most importance.

A preferred aglycosylated antibody with a binding affinity for the CD3 antigen thus has a heavy chain with at least one CDR and particularly three CDRs selected from the amino acid sequences:

(a) Ser-Phe-Pro-Met-Ala (SEQUENCE ID NO. 1), (b) Thr-Ile-Ser-Thr-Ser-Gly-Gly-Arg-Thr-Tyr-Tyr-Arg-Asp-Ser-Val-Lys-Gly (SEQUENCE ID NO. 2), (c) Phe-Arg-Gln-Tyr-Ser-Gly-Gly-Phe-Asp-Tyr (SEQUENCE ID NO. 3), and conservatively modified variants thereof, and/or a light chain with at least one CDR and particularly three CDRs selected from the amino acid sequences:

(d) Thr-Leu-Ser-Ser-Gly-Asn-Ile-Glu-Asn-Asn-Tyr-Val-His (SEQUENCE ID NO. 4), (e) Asp-Asp-Asp-Lys-Arg-Pro-Asp (SEQUENCE ID NO. 5), (f) His-Ser-Tyr-Val-Ser-Ser-Phe-Asn-Val (SEQUENCE ID NO. 6), and conservatively modified variants thereof.

Where an aglycosylated antibody according to the invention contains preferred CDRs as described hereinbefore it conveniently contains both one or more of the specified heavy chain CDRs and one or more of the specified light chain CDRs. The CDRs (a), (b) and (c) are arranged in the heavy chain in the sequence: framework region 1/(a)/framework region 2/(b)/framework region 3/(c)/framework region 4 in a leader→constant domain (n-terminal to C-terminal) direction and the CDRs (d), (e) and (f) are arranged in the light chain in the sequence: framework region 1/(d)/framework region 2/(e)/framework region 3/(f)/framework region 4 in a leader→constant domain direction. It is preferred, therefore, that where all three are present the heavy chain CDRs are arranged in the sequence (a), (b), (c) in a leader→constant domain direction and the light chain CDRs are arranged in the sequence (d), (e), (f) in a leader→constant domain direction.

It should be appreciated however, that aglycosylated antibodies according to the invention may contain quite different CDRs from those described hereinbefore and that, even when this is not the case, it may be possible to have heavy chains and particularly light chains containing only one or two of the CDRs (a), (b) and (c) and (d), (e) and (f), respectively. However, although the presence of all six CDRs defined above is therefore not necessarily required in an aglycosylated antibody according to the present invention, all six CDRs will most usually be present in the most preferred antibodies. A particularly preferred aglycosylated antibody therefore has a heavy chain with three CDRs comprising the amino acid sequences (a), (b) and (c) or conservatively modified variants thereof and a light chain with three CDRs comprising the amino acid sequences (d), (e) and (f) or conservatively modified variants thereof in which the heavy chain CDRs are arranged in the order (a), (b), (c) in the leader constant region direction and the light chain CDRs are arranged in the order (d), (e), (f) in the leader constant region direction.

The CDRs may be of different origin to the variable framework region and/or to the constant region and, since the CDRs will usually be of rat or mouse origin, this is advantageous to avoid an antiglobulin response in the human, although the invention does extend to antibodies with such regions of rat or mouse origin.

More usually the CDRs are either of the same origin as the variable framework region but of a different origin from the constant region, for example in a part human chimaeric antibody, or, more commonly, the CDRs are of different origin from the variable framework region.

The preferred CDRs discussed hereinbefore are obtained from a rat CD3 antibody. Accordingly, although the variable domain framework region can take various forms, it is conveniently of or derived from those of a rodent, for example a rat or mouse, and more preferably of or derived from those of human origin. One possibility is for the antibody to have a variable domain framework region corresponding to that in the YTH12.5 hybridoma although the constant region will still preferably be of or derived from those of human origin. However the antibody of the invention is preferably in the humanised form as regards both the variable domain framework region and as discussed further hereinafter, the constant region.

Accordingly, the invention further comprises an aglycosylated antibody which has a binding affinity for the human CD3 antigen and in which the variable domain framework regions and/or the constant region are of or are derived from those of human origin.

Certain human variable domain framework sequences will be preferable for the grafting of the preferred CDR sequences, since the 3-dimensional conformation of the CDRs will be better maintained in such sequences and the antibody will retain a high level of binding affinity for the antigen. Desirable characteristics in such variable domain frameworks are the presence of key amino acids which maintain the structure of the CDR loops in order to ensure the affinity and specificity of the antibody for the CD3 antigen, the lambda type being preferred for the light chain.

Human variable region frameworks which are particularly suitable for use in conjunction with the above CDRs have been previously identified in UK Patent Application No. 9121126.8. The heavy chain variable (V) region frameworks are those coded for by the human VH type III gene VH26.D.J. which is from the B cell hybridoma cell line 18/2 (Genbank Code: Huminghat, Dersimonian et al., Journal of Immunology, 139, 2496–2501). The light chain variable region frameworks are those of the human $V_L\lambda$ type VI gene SUT (Swissprot code; LV6CSHum, Solomon et al. In Glenner et al (Eds), Amyloidosis, Plenum Press N.Y., 1986, p.449.

The one or more preferred CDRs of the heavy chain of the rat anti-CD3 antibody are therefore preferably present in a human variable domain framework which has the following amino acid sequence reading in the leader→constant region direction, CDR indicating a CDR (a), (b) or (c) as defined hereinbefore, a conservatively modified variant thereof or an alternative CDR:-Glu-Val-Gln-Leu-Leu-Glu-Ser-Gly-Gly-Gly-leu-Val-Gln-Pro-Gly-Gly-Ser-Leu-Arg-Leu-Ser-Cys-Ala-Ala-Ser-Gly-Phe-Thr-Phe-Ser-/CDR/-Trp-Val-Arg-Gln-Ala-Pro-Gly-Lys-Gly-Leu-Glu-Trp-Val-Ser-/CDR/-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-Lys-/CDR/-Trp-Gly-Gln-Gly-Thr-Leu-Val-Thr-Val-Ser-Ser (SEQUENCE ID NO. 7/CDR/ SEQUENCE ID NO. 8/CDR/SEQUENCE ID NO. 9/CDR/ SEQUENCE ID NO. 10).

In an aglycosylated antibody containing all three preferred CDRs, the heavy chain variable region comprises the following sequence:-Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-Ser-Ser-Phe-Pro-Met-Ala-Trp-Val-Arg-Gln-Ala-Pro-Gly-Lys-Gly-Leu-Glu-Trp-Val-Ser-Thr-Ile-Ser-Thr-Ser-Gly-Gly-Arg-Thr-Tyr-Tyr-Arg-Asp-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-Lys-Phe-Arg-Gln-Tyr-Ser-Gly-Gly-Phe-Asp-Tyr-Trp-Gly-Gln-Gly-Thr-Leu-Val-Thr-Val-Ser-Ser (SEQUENCE ID NO. 11).

Similarly, the one or more preferred CDRs of the light chain of the rat CD3 antibody are therefore preferably present in a human variable domain framework which has the following amino acid sequence reading in the leader→constant region direction, CDR indicating a CDR (d), (e) and (f) as defined hereinbefore, a conservatively modified variant thereof or an alternative CDR:-Asp-Phe-Met-Leu-Thr-Gln-Pro-His-Ser-Val-Ser-Glu-Ser-Pro-Gly-Lys-Thr-Val-Ile-Ile-Ser-Cys-/CDR/-Trp-Tyr-Gln-Gln-Arg-Pro-Gly-Arg-Ala-Pro-Thr-Thr-Val-Ile-Phe-/CDR/-Gly-Val-Pro-Asp-Arg-Phe-Ser-Gly-Ser-Ile-Asp-Arg-Ser-Ser-Asn-Ser-Ala-Ser-Leu-Thr-Ile-Ser-Gly-Leu-Gln-Thr-Glu-Asp-Glu-Ala-Asp-Tyr-Tyr-Cys-/CDR/-Phe-Gly-Gly-Gly-Thr-Lys-Leu-Thr-Val-Leu (SEQUENCE ID NO. 12/CDR/ SEQUENCE ID NO. 13/CDR/SEQUENCE ID NO. 14/CDR/SEQUENCE ID NO. 15).

In an aglycosylated antibody containing all three preferred CDRs the light chain variable region comprises the following sequence:-Asp-Phe-Met-Leu-Thr-Gln-Pro-His-Ser-Val-Ser-Glu-Ser-Pro-Gly-Lys-Thr-Val-Ile-Ile-Ser-Cys-Thr-Leu-Ser-Ser-Gly-Asn-Ile-Glu-Asn-Asn-Tyr-Val-His-Trp-Tyr-Gln-Gln-Arg-Pro-Gly-Arg-Ala-Pro-Thr-Thr-Val-Ile-Phe-Asp-Asp-Asp-Lys-Arg-Pro-Asp-Gly-Val-Pro-Asp-Arg-Phe-Ser-Gly-Ser-Ile-Asp-Arg-Ser-Ser-Asn-Ser-Ala-Ser-Leu-Thr-Ile-Ser-Gly-Leu-Gln-Thr-Glu-Asp-Glu-Ala-Asp-Tyr-Tyr-Cys-His-Ser-Tyr-Val-Ser-Ser-Phe-Asn-Val-Phe-Gly-Gly-Gly-Thr-Lys-Leu-Thr-Val-Leu (SEQUENCE ID NO. 16).

The variable domains, for example comprising one or more preferred CDRs as described above, preferably in the humanised form having human antibody-derived variable framework regions, are attached to appropriate constant domains.

The heavy and light chain constant regions can be based on antibodies of different types as desired subject to the antibody being an IgG antibody, but although they may be of or derived from those of rat or mouse origin they are preferably of or are derived from those of human origin. For the light chain the constant region is preferably of the lambda type and for the heavy chain it is preferably of an IgG isotype, especially IgG1, modified to effect aglycosylation as appropriate. All human constant regions of the IgG isotype are known to be glycosylated at the asparagine residue at position 297, which makes up part of the N-glycosylation motif Asparagine$^{297}$-X$^{298}$-Serine$^{299}$ or Threonine$^{299}$, where X is the residue of any amino acid except proline. The antibody of the invention may thus be aglycosylated by the replacement of Asparagine$^{297}$ in such a constant region with another amino acid which cannot be glycosylated. Any other amino acid residue can potentially be used, but alanine is the most preferred. Alternatively, glycosylation at Asparagine$^{297}$ can be prevented by altering one of the other residues of the motif, e.g. by replacing residue 298 by proline, or residue 299 by any amino acid other than serine or threonine. Techniques for performing this site directed mutagenesis are well known to those skilled in the art and may for example be performed using a site directed mutagenesis kit such, for example, as that commercially available from Amersham. The procedure is further exemplified hereinafter.

It is well recognised in the art that the replacement of one amino acid in a CDR with another amino acid having similar properties, for example the replacement of a glutamic acid residue with an aspartic acid residue, may not substantially alter the properties or structure of the peptide or protein in which the substitution or substitutions were made. Thus, the aglycosylated antibodies of the present invention include those antibodies containing the preferred CDRs but with a specified amino acid sequence in which such a substitution or substitutions have occurred without substantially altering the binding affinity and specificity of the CDRs. Alternatively, deletions may be made in the amino acid residue sequence of the CDRs or the sequences may be extended at one or both of the N- and C-termini whilst still retaining activity.

Preferred aglycosylated antibodies according to the present invention are such that the affinity constant for the antigen is $10^5$ mole$^{-1}$ or more, for example up to $10^{12}$ mole$^{-1}$. Ligands of different affinities may be suitable for different uses so that, for example, an affinity of $10^6$, $10^7$ or $10^8$ mole$^{-1}$ or more may be appropriate in some cases. However antibodies with an affinity in the range of $10^6$ to $10^8$ mole$^{-1}$ will often be suitable. Conveniently the antibodies also do not exhibit any substantial binding affinity for other antigens. Binding affinities of the antibody and antibody specificity may be tested by assay procedures such as those described in the Examples section hereinafter, (Effector Cell Retargetting Assay), or by techniques such as ELLSA and other immunoassays.

Antibodies according to the invention are aglycosylated IgG CD3 antibodies having a "Y" shaped configuration which may have two identical light and two identical heavy chains and are thus bivalent with each antigen binding site having an affinity for the CD3 antigen. Alternatively, the invention is also applicable to antibodies in which only one of the arms of the antibody has a binding affinity for the CD3 antigen. Such antibodies may take various forms. Thus the other arm of the antibody may have a binding affinity for an antigen other than CD3 so that the antibody is a bispecific antibody, for example as described in U.S. Pat. No. 4,474,893 and European Patent Applications Nos. 87907123.1 and 87907124.9. Alternatively, the antibody may have only one arm which exhibits a binding affinity, such an antibody being termed "monovalent".

Monovalent antibodies (or antibody fragments) may be prepared in a number of ways. Glennie and Stevenson (Nature, 295, 712–713, (1982)) describe a method of preparing monovalent antibodies by enzymic digestion. Stevenson et al. describe a second approach to monovalent antibody preparation in which enzymatically produced Fab' and Fc fragments are chemically cross-linked (Anticancer Drug Design, 3, 219–230 (1989)). In these methods the resulting monovalent antibodies have lost one of their Fab' arms. A third method of preparing monovalent antibodies is described in European Patent No. 131424. In this approach the "Y" shape of the antibody is maintained, but only one of the two Fab' domains will bind to the antigen. This is achieved by introducing into the hybridoma a gene coding for an irrelevant light chain which will combine with the heavy chain of the antibody to produce a mixture of products in which the monovalent antibody is the one of interest.

More preferably, however, the monovalent aglycosylated CD3 antibodies of the invention are prepared by the following method. This involves the introduction into a suitable expression system, for example a cell system as described hereinafter, together with genes coding for the heavy and light chains, of a gene coding for a truncated heavy chain in which the variable region domain and first constant region domain of the heavy chain are absent, the gene lacking the exon for each of these domains. This results in the production by the cell system of a mixture of (a) antibodies which are complete bivalent antibodies, (b) antibody fragments consisting only of two truncated heavy chains (i.e. an Fc fragment) and (c) fragments of antibody which are monovalent for the CD3 antigen, consisting of a truncated heavy chain and a light chain in association with the normal heavy chain. Such an antibody fragment (c) is monovalent since it has any only one Fab' arm. Production of a monovalent antibody in the form of such a fragment by this method is preferred for a number of reasons. Thus, the resulting antibody fragment is easy to purify from a mixture of antibodies produced by the cell system since, for example, it may be separable simply on the basis of its molecular weight. This is not possible in the method of European Patent No. 131424 where the monovalent antibody produced has similar characteristics to a bivalent antibody in its size and outward appearance. Additionally, the production of a monovalent antibody fragment by the new method uses conditions which can more easily be controlled and is thus not as haphazard as an enzyme digestion/chemical coupling procedure which requires the separation of a complex reaction product, with the additional advantage that the cell line used will continue to produce monovalent antibody fragments, without the need for continuous synthesis procedures as required in the enzyme digestion/chemical coupling procedure.

It is believed that aglycosylated antibodies according to the invention do not occur in nature and these aglycosylated antibodies may in general be produced synthetically in a number of ways. Most conveniently, however, appropriate gene constructs for the constant and variable regions of the heavy and light chains which are present in the antibody are separately obtained and then inserted in a suitable expression system.

Genes encoding the variable domains of a ligand of the desired structure may be produced and conveniently attached to genes encoding the constant domains of an antibody which have undergone site directed mutagenesis. These constant genes may be obtained from hybridoma cDNA or from the chromosomal DNA and have undergone mutagenesis (site directed) to produce the aglycosylated constant regions. Genes encoding the variable regions may also be derived by gene synthesis techniques used in the identification of the CDRs contained herein. Suitable cloning vehicles for the DNA may be of various types.

Expression of these genes through culture of a cell system to produce a functional CD3 ligand is most conveniently effected by transforming a suitable prokaryotic or particularly eukaryotic cell system, particularly an immortalised mammalian cell line such as a myeloma cell line, for example the YB2/3.01/Ag20 (hereinafter referred to as Y0) rat myeloma cell, or Chinese hamster ovary cells (although the use of plant cells is also of interest), with expression vectors which include DNA coding for the various antibody regions, and then culturing the transformed cell system to produce the desired antibody. Such general techniques of use for the manufacture of ligands according to the present invention are well known in the very considerable art of genetic engineering and are described in publications such as "Molecular Cloning" by Sambrook, Fritsch and Maniatis, Cold Spring Harbour Laboratory Press, 1989 (2nd edition). The techniques are further illustrated by the Examples contained herein.

The present invention thus includes a process for the preparation of an aglycosylated IgG antibody having a binding affinity for the CD3 antigen which comprises culturing cells capable of expressing the antibody in order to effect expression thereof. The invention also includes a cell line which expresses an aglycosylated antibody according to the invention.

Preferred among such cell lines are those which comprise DNA sequences encoding the preferred CDRs described hereinbefore. A group of nucleotide sequences coding for the CDRs (a) to (f) described hereinbefore is as indicated under (a) to (f) below, respectively, but it will be appreciated that the degeneracy of the genetic code permits variations to be made in these sequences whilst still encoding for the CDRs' amino acid sequences.

(a) AGCTTTCCAA TGGCC (SEQUENCE ID NO. 17)
(b) ACCATTAGTA CTAGTGGTGG TAGAACTTAC TATCGAGACT CCGTGAAGGG C (SEQUENCE ID NO. 18)
(c) TTTTCGGCAGT ACAGTGGTGG CTTTGATTAC (SEQUENCE ID NO. 19)
(d) ACACTCAGCT CTGGTAACAT AGAAAACAAC TATGTGCAC (SEQUENCE ID NO. 20)
(e) GATGATGATA AGAGACCGGA T (SEQUENCE ID NO. 21)
(f) CATTCTTATG TTAGTAGTTT TAATGTT (SEQUENCE ID NO. 22)

Such cell lines will particularly contain larger DNA sequences which comprise (1) DNA expressing human heavy chain variable framework regions and one or more of (a), (b) and (c), and (2) DNA expressing human light chain variable framework regions and one or more of (d), (e) and (f). A specific example of such DNA is that sequenced(1) indicated below which codes for the CDRs (a), (b) and (c) arranged in the heavy chain framework coded for by the human VH type III gene VH26.D.J. as discussed hereinbefore and that sequence (2) indicated below which codes for the CDRs (d), (e) and (f) arranged in the light chain framework coded for by the human $V_L\lambda$ type VI gene SUT. The CDR sequences (a), (b), (c), (d), (e) and (f) have been underlined.

(1) GAGGTCCAAC TGCTGGAGTC TGGGGGCGGT TTAGTGCAGC CTGGAGGGTC CCTGAGACTC TCCTGTGCAG CCTCAGGATT CACTTTCAGT <u>AGCTTTCCAATGGCC</u>TGGGT CCGCCAGGCT CCAGGGAAGG GTCTGGAGTG GGTCTCA <u>ACCATTAGTACTA GTGGTGGTAG AACTTACTAT CGAGACTCCG TGAAGGGCCG</u> ATTCACTATC TCCAGAGATA ATAGCAAAAA TACCCTATAC CTGCAAATGA ATAGTCTGAG GGCTGAGGAC ACGGCCGTCT AlTACTGTGC AAAA <u>TTTCGGCAGTACAGTG GTGGCTTTGA TTACTG</u> GGGC CAAGGGACCC TGGTCACCG CTCCTCA (SEQUENCE ID NO. 23)

(2) GACTTCATGC TGACTCAGCC CCACTCTGTG TCTGAGTCTC CCGGAAAGAC AGTCATTATT TCTTGC <u>ACAC TCAGCTCTGG TAACATAGAA AACAAC TATGTGCACTGGTA</u> CCAGCAAAGGCCGGGAAGAGCTCCCAC- CACTGTGATTTTC <u>GATGATGATA AGAGACCGGA</u> TGGTGTCCCT GACAGGTTCT CTGGCTCCAT TGACAGGTCT TCCAACTCAG CCTCCCTGAC AATCAGTGGT CTGCAAACTG AAGATGAAGC TGACTACTAC TGT<u>CATTCTT ATGTTAGTAG TTTTAATGTT</u> TTCGGCGGTG GAACAAAGCT CACTGTCCTT (SEQUENCE ID NO. 24)

The cell lines will of course also particularly contain DNA sequences expressing the heavy and light chain constant regions.

The humanised aglycosylated antibodies in accordance with the invention have therapeutic value. In particular, such aglycosylated antibodies, especially a humanised aglycosylated antibody with a specificity for the human CD3 antigen, has valuable applications in immunosuppression, particularly in the control of graft rejection, where it is especially desirable that immunosuppression is temporary rather than total, and thus that T-cells are not completely destroyed, but instead rendered non-functional by antibody blockade of the CD3 antigen—TCR complex. In addition, the aglycosylated CD3 antibodies may have potential in other areas such as in the treatment of cancer, specifically in the construction of bispecific antibodies (for effector cell retargetting) or antibody-toxin conjugates, where the efficacy of the therapeutic agent would be compromised by Fc-mediated killing of the effector cells or non-specific killing of Fc receptor bearing cells respectively.

In a further aspect, the invention thus includes a method of treating patients with cancer, particularly a lymphoma, or for immunosuppression purposes, for instance in a case where graft rejection may occur, comprising administering a therapeutically effective amount of an aglycosylated antibody in accordance with the invention.

Aglycosylated antibodies in accordance with the invention may be formulated for administration to patients by administering the said antibody together with a physiologically acceptable diluent or carrier. The antibodies are preferably administered in an injectable form together with such a diluent or carrier which is sterile and pyrogen free. By way of guidance it may be stated that a suitable dose of antibody is about 1–10 mg injected daily over a time period of, for example 10 days, although due to the elimination of the first dose response it will be possible if desired to adminster higher amounts of the antibody, for example even up to 100 mg daily, depending on the individual patient's needs. Veterinary use is on a similar g/kg dosage basis.

BRIEF DESCRIPTION OF THE DRAWINGS.

The invention is illustrated by the following Examples which are illustrated by the drawings listed below.

EXAMPLES

Example 1

Figure 1:
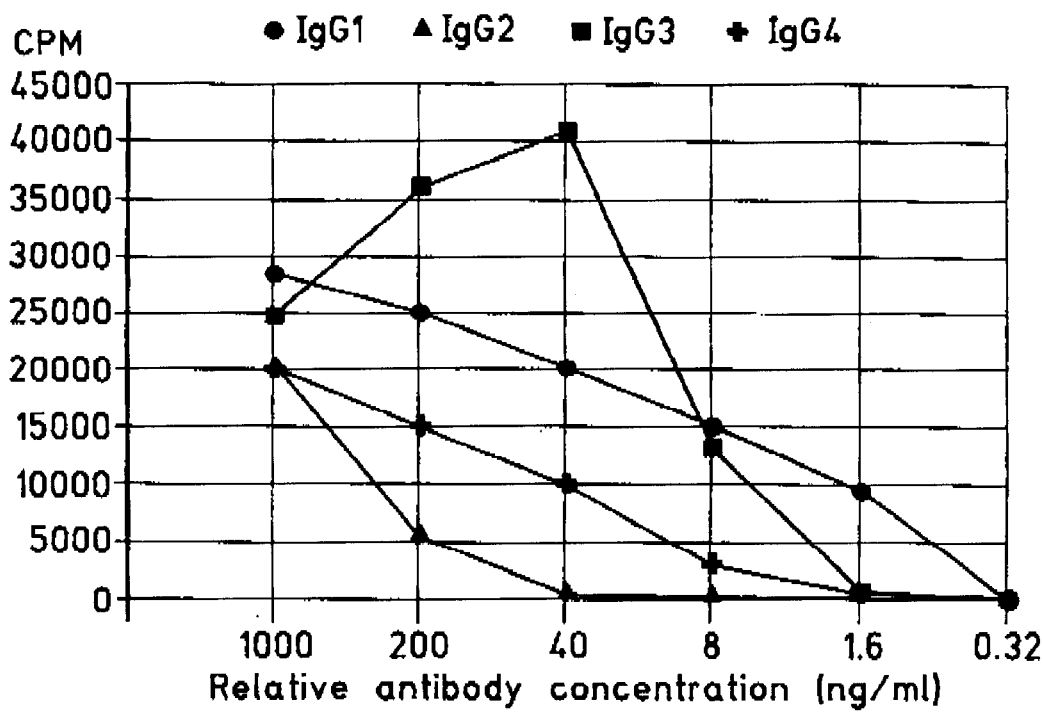
FIGS. 1–8: These figures show the results of proliferation assays of peripheral blood lymphocytes to CD3 antibodies. Four different healthy volunteers were used. The humanised anti-lymphocyte antibody CDw52 was included as a negative control.
Figure 2:
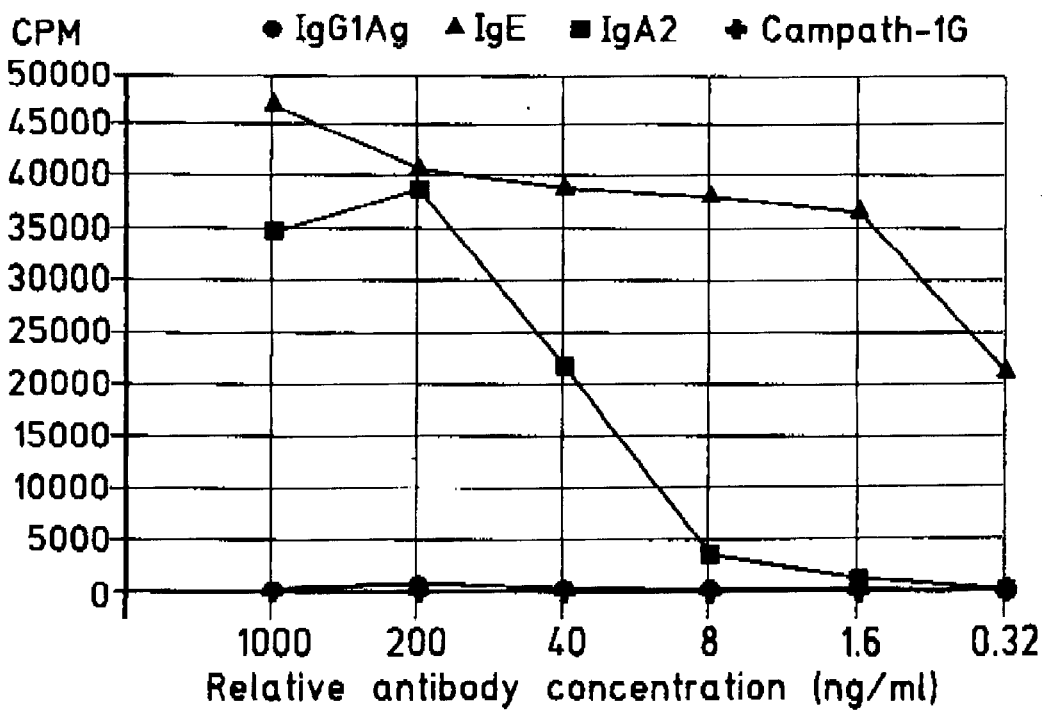
Figure 3:
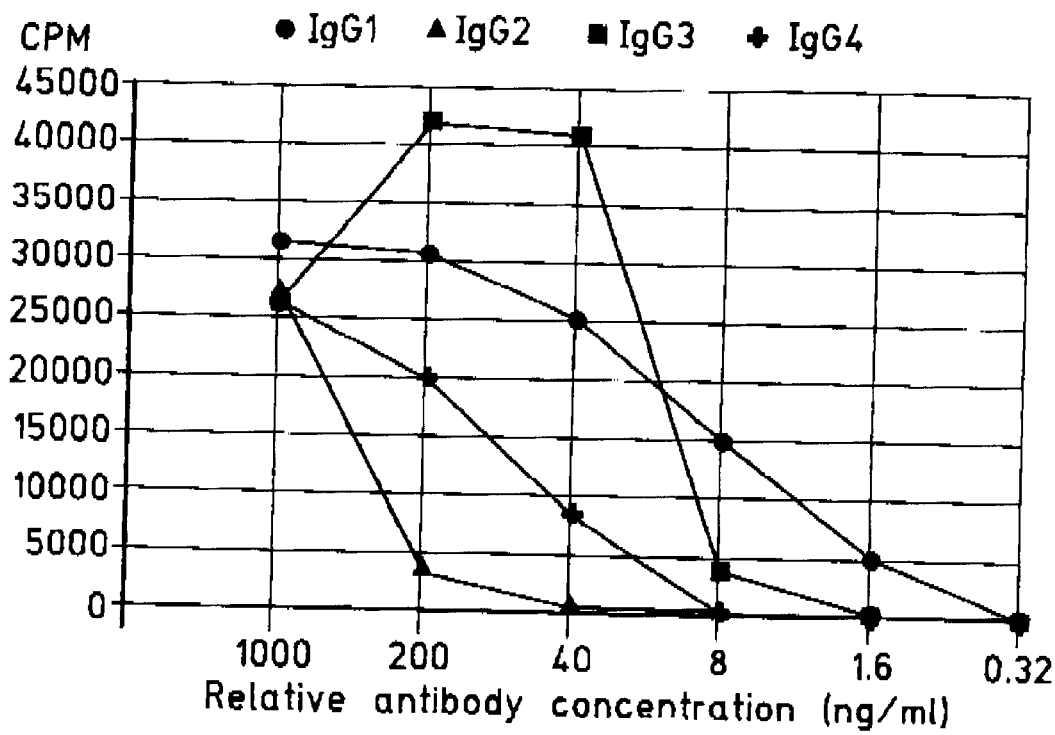
Figure 4:
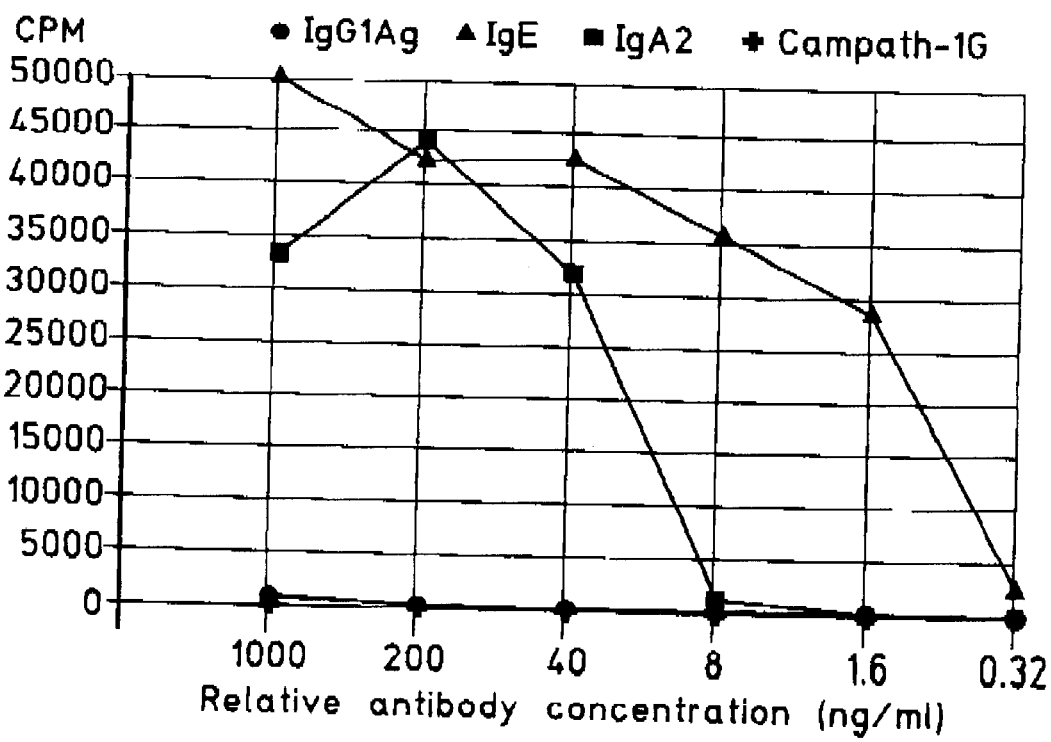
Figure 5:
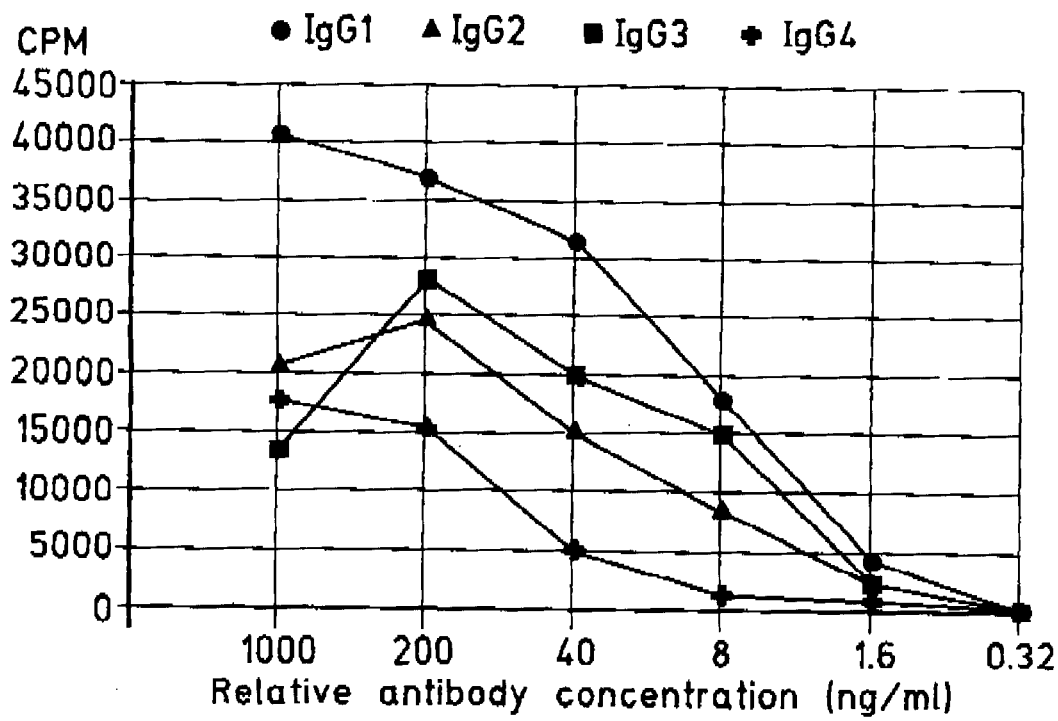
Figure 6:
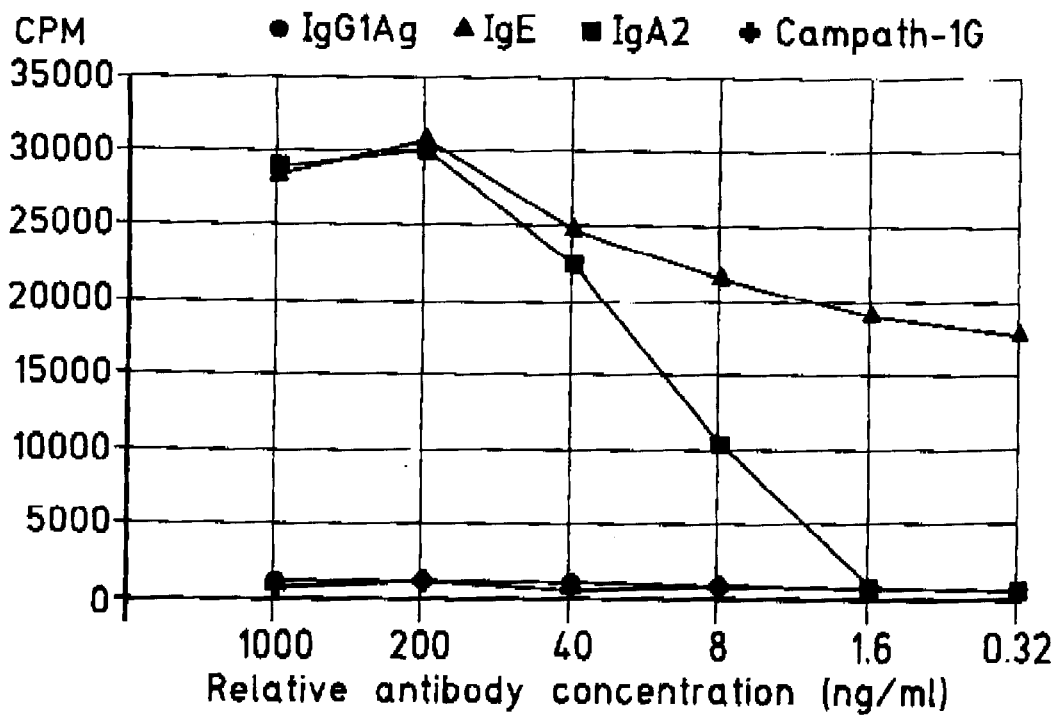
Figure 7:
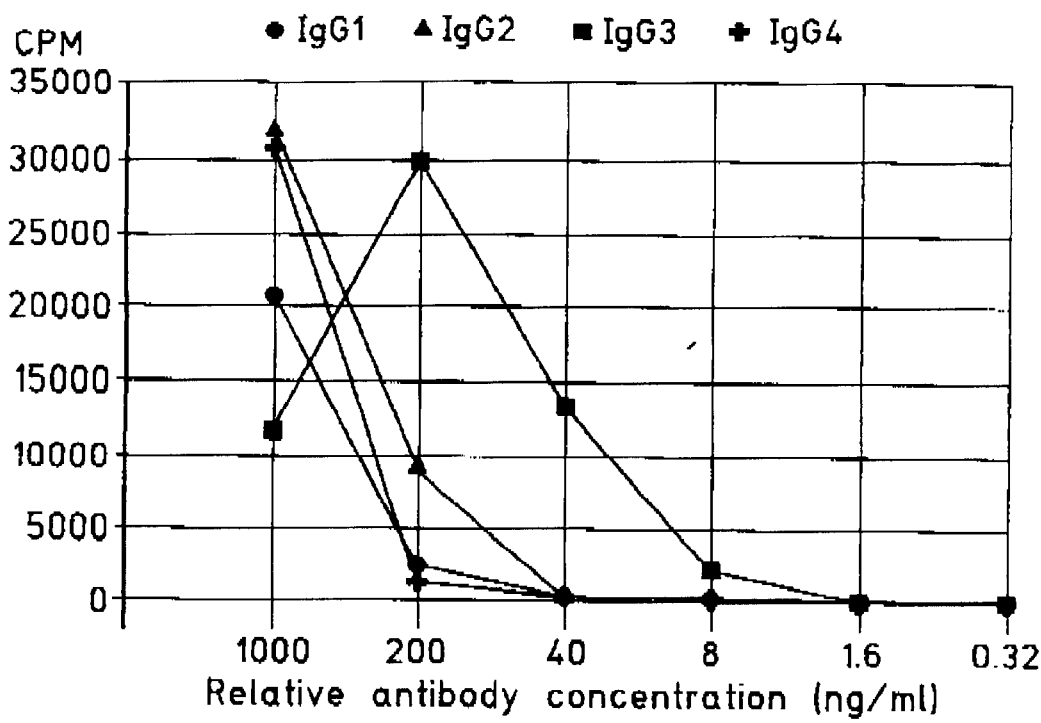
Figure 8:
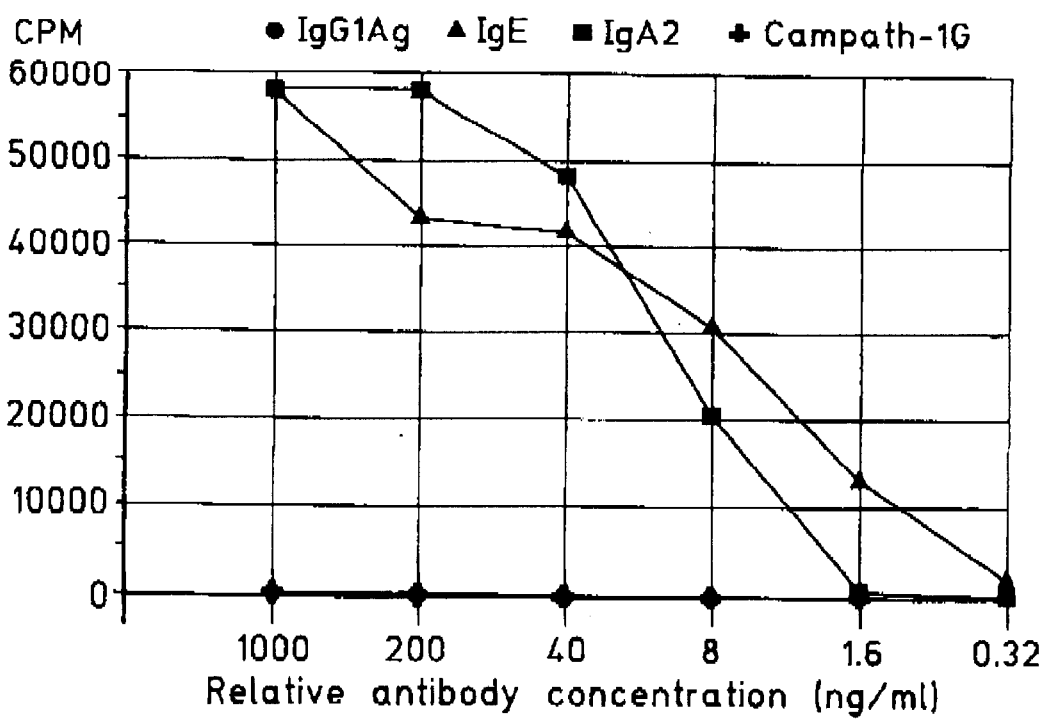

Preparation of an Aglycosylated Antibody Specific for the Human CD3 Antigen Containing CDRs From the YTH 12.5 rat Antibody in Human Variable Framework Regions The cloning and re-shaping of the V-region gene of the rat antibody YTH 12.5 specific for the human CD3 antigen was performed as described in Routledge et al., 1991, Eur. J. Immunol., 21, 2717 and in UK Patent Application No. 9121126.8 and its equivalents. YTH 12.5 is a rat hybridoma cell line secreting an IgG2b monoclonal antibody specific for the CD3 antigen complex.

Briefly, the methodology was based on that of Orlandi et al., 1989, PNAS USA, 86, 3833, using the polymerase chain reaction (PCR). The $V_H$ gene (heavy chain variable region gene) was cloned using oligonucleotide primers VH1FOR and VH1BACK. The PCR products were ligated into the vector M13-VHPCR1 in which site directed mutagenesis was performed using 6 oligonucleotide primers. The $V_L$ gene (light chain variable region gene) was cloned using primers designed based on the published $V_L\lambda$ sequences. The gene was cloned into the vector M13-VKPCR, together with the human lambda light chain constant region. In this vector mutagenesis of the $V_L$ framework was performed using 5 oligonucleotides. The humanised $V_L$ gene was then inserted into the expression vector pHβApr-1.

A vector was generated (p316) in which the reshaped CD3 VH gene could be expressed in conjunction with different immunoglobulin H chain constant region genes, this vector being based on the pHβApr-gpt vector (Gunning et al., 1987, P.N.A.S. USA, 85, 7719–7723). A 1.65 Kb fragment of DNA carrying the dihydrofolate reductase (dhft) gene and SV 40 expression signals (Page & Sydenham, 1991, Biotechnology, 9, 64) was inserted into the unique EcoRI site of pHoApr-gpt. A 700 bp HindIII-BamHI DNA fragment encoding the reshaped CD3-VH gene was then cloned into the vector's multiple cloning site, downstream and under the control of the β actin promoter. The desired H chain constant region gene (in genomic configuration) could then be inserted into the unique BamHI restriction enzyme site downstream of the CD3-VH gene.

The aglycosyl human IgG1 constant region was derived from the wild type Glm (1,17) gene described by Takahashi et al., (1982, Cell, 29, 671–679) as follows. The gene was cloned into the vector M13 tg131 where site-directed mutagenesis was performed (Amersham International PLC) to mutate the amino acid residue at position 297 from an asparagine to an alanine residue.

Oligosaccharide at Asn-297 is a characteristic feature of all normal human IgG antibodies (Kabat et al., 1987, Sequence of Proteins of Immunological Interest, U.S. Department of Health human Services Publication), each of the two heavy chains in the IgG molecules having a single branched chain carbohydrate group which is linked to the amide group of the asparagine residue (Rademacher and Dwek, 1984, Prog. Immunol., 5, 95–112). Substitution of asparagine with alanine prevents the glycosylation of the antibody.

The 2.3 Kb aglycosyl IgG1 constant region was excised from M13 by double digestion using BamHI and BglII and ligated into the BamHI site of vector p316 to produce clone p323.

Subconfluent monolayers of dhfr⁻ Chinese Hamster Ovary cells were co-transfected with the vector p323 containing the heavy chain gene and a second vector p274 containing the re-shaped human λ light chain (Routledge et al., 1991, Eur. J. Immunol., 21, 2717–2725). Prior to tranfection both plasmid DNAs were linearised using the restriction endonuclease PvuI. Transfection was carried out using the DOTMA reagent (Boehringer, Germany) following the manufacturer's recommendations.

Heavy and light chain transfectants were selected for in xanthine/hypoxanthine free IMDM containing 5% (v/v) dialysed foetal calf serum.

The production of the analogous wild type human IgG1-CD3 heavy chain vector p278 has been described elsewhere (Routledge et al., 1991, Eur. J. Immunol., 21, 2717–2725). H-chain expression vectors carrying the non-mutant human IgG2 (Flanagan & Rabbitts, 1982, Nature 300, 709–713), IgG3 (Huck et al., 1986, Nuc. Acid. Res., 14, 1779–1789), IgG4 (Flanagan & Rabbitts, 1982, Nature 300, 709–713), Epsilon (Flanagan & Rabbitts, 1982, EMBO. Journal 1, 655–660) and Alpha-2 (Flanagan & Rabbitts, 1982, Nature 300, 709–713) constant region genes (vectors p317, p318, p320, p321 and p325, respectively) were derived from the vector p316. Introduction of these vectors, in conjunction with the light chain vector p274, into dhfr⁻ CHO cells as described earlier, produced cell lines secreting CD3 antibody of the γ1, γ2, γ3, γ4, ε and α-2 isotype respectively. Cells expressing CD3 antibodies were subjected to two rounds of cloning in soft agar, and then expanded into roller bottle cultures. The immunoglobulin from approximately 4 litres of tissue culture supernatant from each cell line was concentrated by ammonium sulphate precipitation, dialysed extensively against PBS and then quantified as follows:

As the antibody was not pure, a competition assay was designed to specifically quantitate the concentration of antibody with CD3 antigen binding capacity. Human T-cell blasts were incubated with FITC labelled UCHT-1, an antibody which binds to the same epitope of the CD3 antigen as the chimaeric panel. The concentration of FITC reagent used had previously been determined to be half saturating. Unlabelled YTH 12.5 (HPLC purified) was titrated from a known starting concentration and added to wells containing T-cells and UCHT-1 FITC. The unlabelled antibody serves as a competitor for the antigen binding site. This is detected as decrease in the mean fluorescence seen when the cells are studied using FACS analysis. Thus, titration of the chimaeric antibodies from unknown starting concentrations yields a series of sigmoidal curves when mean fluorescence is plotted against antibody dilution. These can be directly compared with the standard YTH 12.5 curve.

Example 2

Proliferation Assays

The capacity of a CD3 antibody to support T-cell proliferation in solution is related to the interaction of the Fc region of the antibody with Fc receptors on accessory cells.

The aglycosylated chimaeric CD3 antibody prepared as described in Example 1 was compared with a panel of other chimaeric antibodies which shared the same variable region architecture but different H chain constant regions (see Example 1) for the ability to induce proliferation of human peripheral blood lymphocytes, Lymphocytes isolated from healthy donors' blood were separated on a lymphopaque gradient, washed and resuspended in IMDM containing 5% (v/v) heat-inactivated human AB serum and plated at $5\times10^4$ to $\times10^5$ cells per well in plates containing CD3 antibodies in solution. After 3 days in culture the cells were pulse labelled with tritiated thymidine and harvested 6 hours later and the level of cellular $^3H$ incorporation was determined by scintillation counting. The proliferation response to titrated antibody was studied in four blood donors. For a fifth donor the proliferation response was studied only at 1 μg. The results are shown in FIGS. 1 to 8.

For the donors studied, all 'wild type' antibodies led to T-cell proliferation. However the mutant, aglycosylated IgG1 isotype was never mitogenic implicating an important role for the carbohydrate side chains.

In a separate experiment, the ability of a panel of CD3 monoclonal antibodies in solution to stimulate T-cell mitogenesis was studied using lymphocytes isolated from the blood of 10 donors from a variety of ethnic backgrounds. All of the naturally occurring isotypes caused proliferation in the presence of 5% human AB serum, although there were T-cell donor dependent variations in the extent of the responses caused by the antibodies. In general, the γ1 and ε monoclonal antibodies were the most mitogenic, activating cells at the lowest concentration, and the γ3 and γ2 were the least active. The aglycosyl derivative of the γ1 monoclonal antibody was the only CD3 antibody which consistently failed to induce T-cell proliferation in any of the donors tested, giving responses equivalent to those of the non-activating control monoclonal antibody Campath-1H. In order to exclude endotoxin contamination as the cause of the proliferation seen with the α2 and ε preparations, it was confirmed that proliferation could be blocked by the addition of an excess of the aglycosyl CD3 mAb thus implicating the CD3 antigen in the activation process.

The total lack of proliferative response seen with the aglycosyl γ1 CD3 monoclonal antibody was surprising, given its position in the ECR activity hierarchy (see Example 5 below). The reason for this inactivity is probably due to its reduced affinity for FcRs rather than because aglycosylation has abolished the ability to trigger some post-binding event required for proliferation, e.g. by destroying a secondary recognition site on the monoclonal antibody. This is supported by the observation that the aglycosyl γ1 mAb could stimulate proliferation to a considerable degree if the assay was performed in IgG-free medium. There is probably a minimum thereshold level for the number of contacts or strength of interaction between T-cell and accessory cell which must be exceeded before proliferation can be initiated, and this cannot be achieved by the aglycosyl γ1 mAb in the presence of significant levels of competing immunoglobulin.

Example 3

The Effect of Chimaeric CD3 Antibodies in Mixed Lymphocyte Reactions

A series of experiments was conducted to test whether the aglycosylated antibody IgG1Ag of Example 1 had the capacity to block T-cell proliferation in a mixed lymphocyte reaction (MLR) and the results of 2 experiments are shown in FIGS. 9 to 12.

Figure 9:
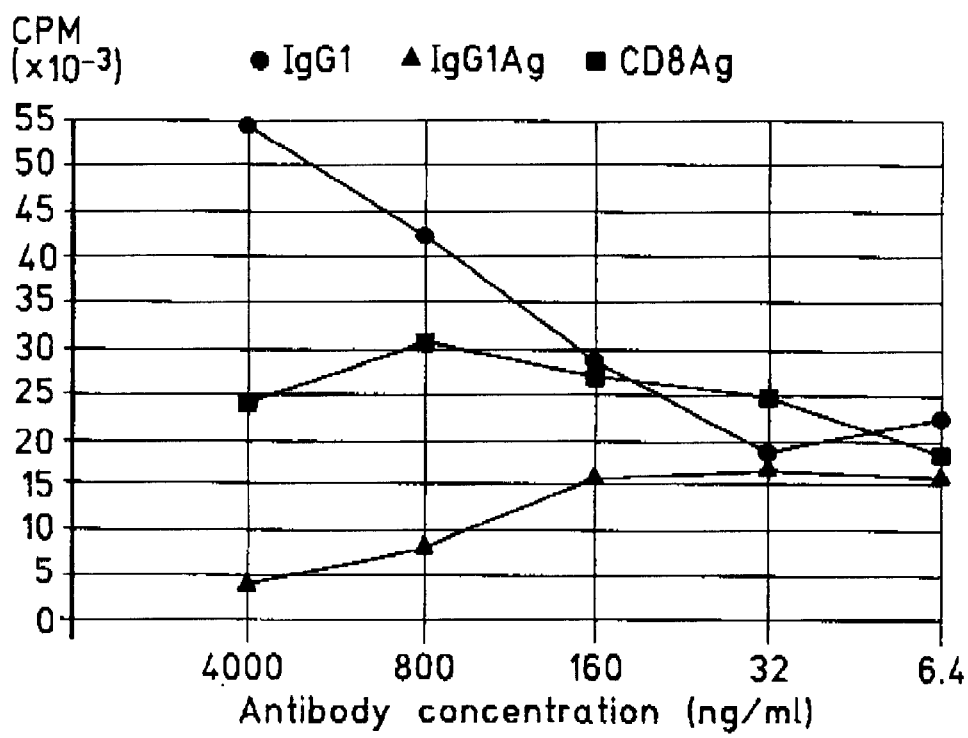
FIGS. 9–12: These figures show the comparison of aglycosylated CD3 antibody and glycosylated CD3 antibody in a mixed lymphocyte reaction. Aglycosylated antibody specific for the mouse CD8 antigen was included as a negative control.
Figure 10:
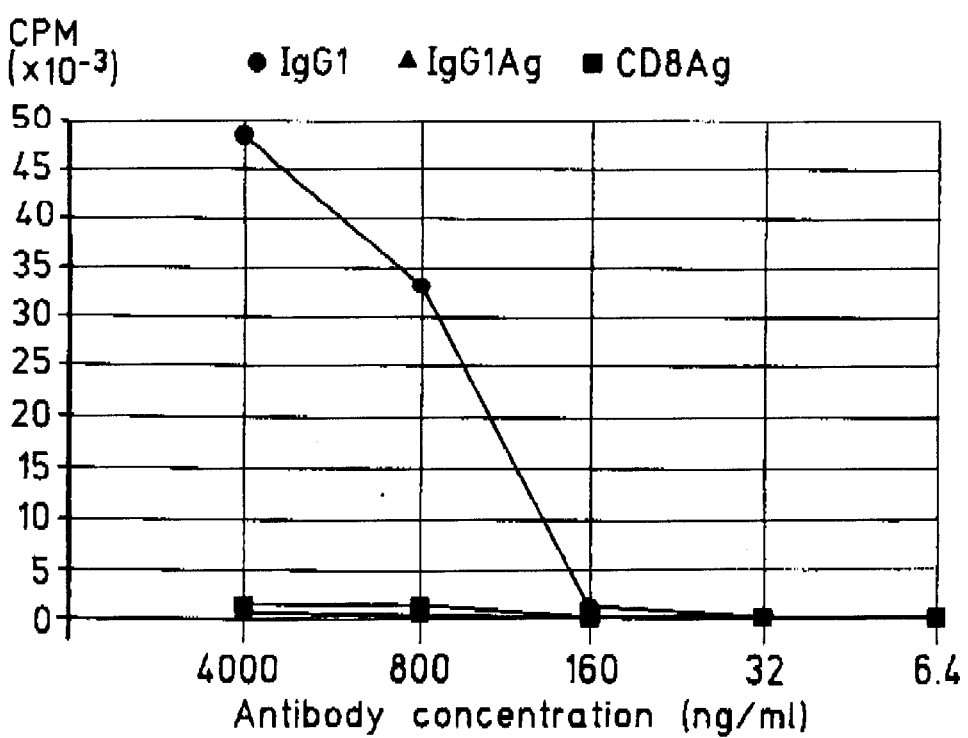
Figure 11:
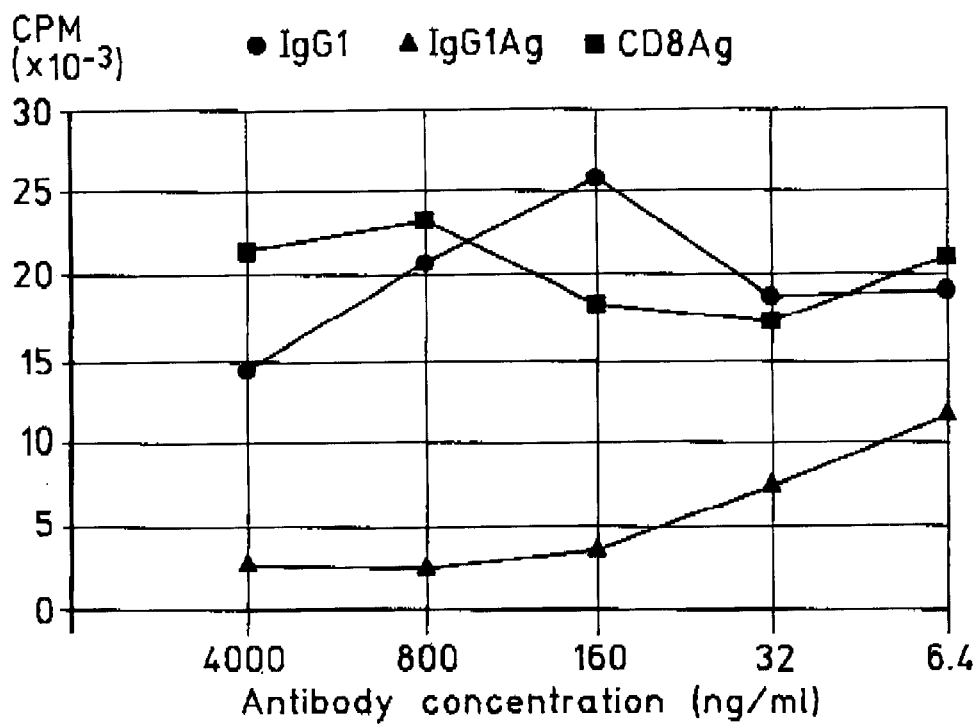
Figure 12:
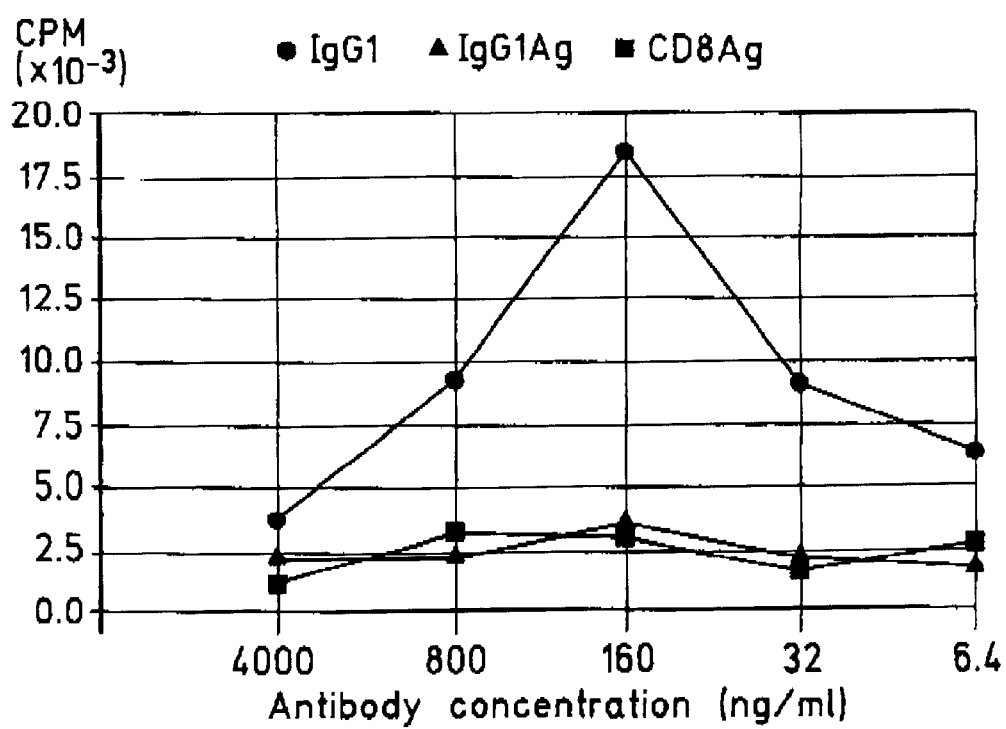

Peripheral blood lymphocytes were isolated from two blood donors. The stimulator cell population was caesium irradiated. The responder population was incubated with titrated antibody for 30 minutes before the irradiated stimulator cells were added (FIGS. 9, 10 and 11). Control wells of responder cells were also incubated with irradiated responder cells at each antibody condition, to determine the specific effect of the antibody on the responder cells (FIGS. 9, 10 and 12).

After 5 days incubation the wells were pulse labelled with tritiated thymidine and harvested 6 hours later.

The aglycosylated antibody does block the mixed lymphocyte reaction; as the antibody is titrated out the blockade effect is less and the proliferation increases. The 'wild type' IgG1 actually has a mitogenic effect on the T-cells and so any blockade of the MLR is not seen through this response.

An 'irrelevant' aglycosylated antibody specific for the murine CD8 antigen was included as a negative control. This antibody has as expected no effect on the MLR.

Example 4

In Vivo Effect of IgG1 Antibodies

In vivo experiments were performed with chimaeric anti-human CD3 antibodies in mice which were transgenic for the human CD3 epsilon subunit including the aglycosylated antibody of Example 1 (IgG1Ag). The ability of some of the chimaeric CD3 antibodies to cause the release of TNF factor following a single injection was compared.

In this set of experiments serum was collected from the mice before injection and then at 90 minutes and 4 hours following intravenous injection with 10 μg of relevant CD3 antibody. Groups consisted of 5 mice and the serum collected from each group was pooled. Analysis of the level of TNF in the serum was performed in the laboratory of Professor Jean-Francois Bach, using a bioassay which measured the cytotoxic effect of sera on the L929 mouse fibroblast cells as a result of the presence of TNF.

The results are shown in Table 1 below:

TABLE 1

TNF detected in serum of hCD3 mice following injection with chimaeric CD3 antibodies

| Sample | Prebleed TNF level | 90 minute TNF level | 4 hour TNF level |
| --- | --- | --- | --- |
| Saline | 0 units/ml | 0 units/ml | 0 units/ml |
| IgG1 | 0 units/ml | >400 units/ml | 0 units/ml |
| IgG2 | 0 units/ml | >400 units/ml | 0 units/ml |
| IgG1Ag | 0 units/ml | 50 units/ml | 0 units/ml |
| IgE | 0 units/ml | 50 units/ml | 25 units/ml |
| YTH 12.5 | 0 units/ml | 50 units/ml | 0 units/ml |

A significant difference is seen between the level of TNF associated with injection of the two forms of human IgG1. The aglycosylated form is associated with at least an eight-fold less release of TNF than the wild type IgG1, or with the IgG2 antibody.

The results of Examples 2–4 show that the aglycosylated CD3 antibody was not mitogenic to T-cells in solution indicating that the antibody had a reduced capacity to interact with Fc receptors on accessory cells. The antibody retained the immunosuppressive properties that are characteristic of CD3 antibodies. In vivo the aglycosylated antibody led to a significantly lower release of tumour necrosis factor in human CD3 transgenic mice than the parental IgG1 antibody. Thus this agent may be an 'improved' CD3 antibody for the purposes of immunosuppression if the decreased TNF release seen in mice is mirrored in humans.

Example 5

Effector Cell Retargetting Assays for the Detection of CD3 Antibodies With the Ability to Direct T-cell Killing This was performed as described elsewhere (Gilliland et al., 1988, PNAS USA, 85, 4419) and measures the ability of a CD3 monoclonal antibody to cross-link activated T-cells to FcγR bearing target cells and thus to mediate target cell lysis. Briefly U937 human monocytic human cells which express the Fcγ receptors I, II and III were labelled with 5 Cr sodium chromate and resuspended to $2\times10^5$ cells per ml. These cells were used as targets. Human T cell blasts, generated from human peripheral blood lymphocytes by activation with mitogenic CD3 antibody followed by culture in medium containing IL-2, were used as the effector cells. They were washed and resuspended at a concentration of $2\times10^5$ cells ml$^-$ prior to use in the assay. 100 μl volumes of the purified chimaeric antibody preparations were diluted in 3-fold steps in the wells of a microtitre plate. 50 μl each of, the effector and target cells were then added to each well and the mixture was, incubated at 37° C. for at least 4 hours. After this time 100 μl of supernatant was removed and assayed for released $^{51}$Cr. Each antibody dilution was tested in duplicate.

Figure 13:
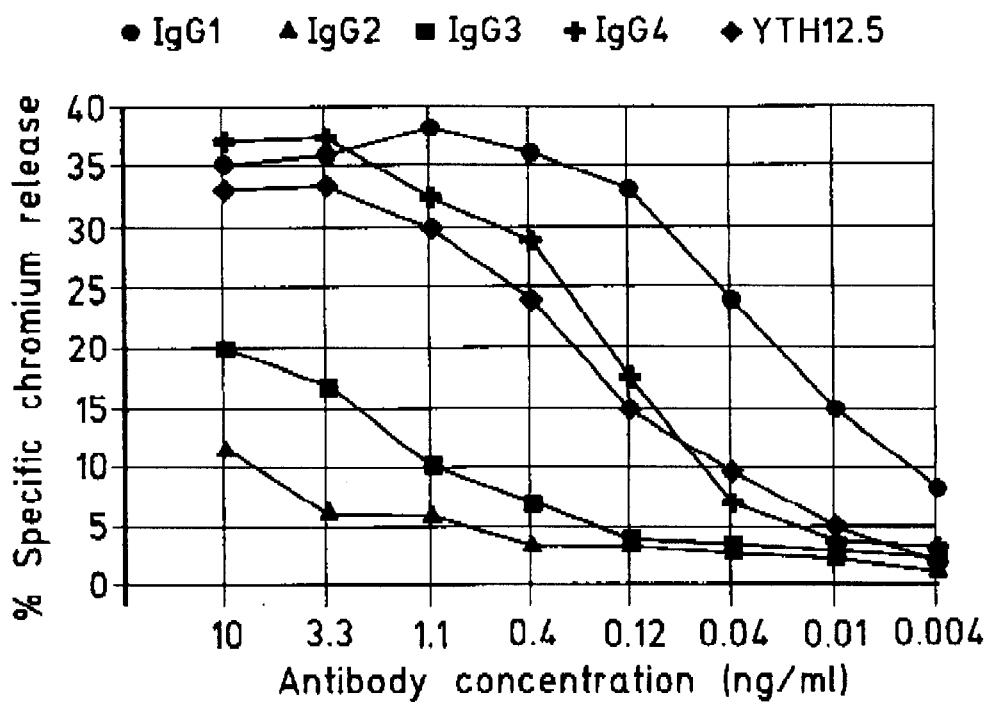
FIGS. 13 & 14: These figures show the results of an Effector Cell Retargetting Assay comparing glycosylated and aglycosylated IgG-type CD3 antibodies. The CDw52 antibody was used as a negative control.
Figure 14:
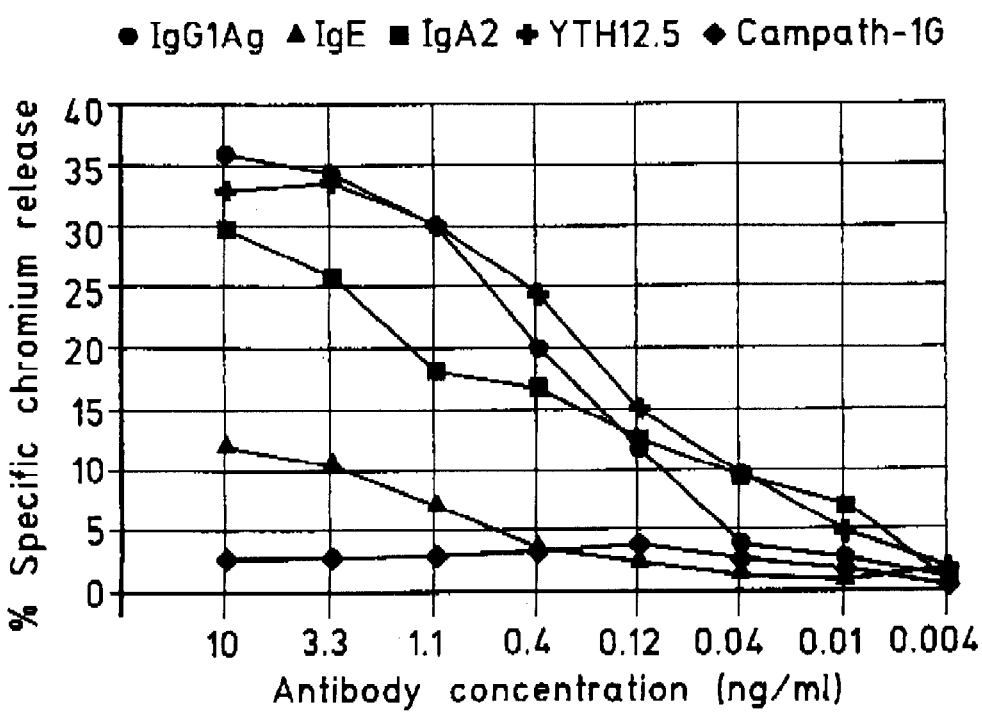

The U937 monocytic cell line expresses human Fc receptors and can be lysed by activated human T-cell blasts in the presence of CD3 monoclonal antibodies capable of cross-linking the two cell types. The results (FIGS. 13 and 14) show that when aglycosylated, the human IgG1 antibody of Example 1 is still able to cross-link 1-cells to the U937 cells, albeit at a reduced level, and thus redirect 1-cell cytotoxicity. This was a surprising finding since, given the published data, the effective killing mediated by aglycosyl γ1 monoclonal antibody was unexpected.

There existed the possibility that removal of the carbohydrate had made this monoclonal antibody especially sticky, and so able to bind to U937 cells without interacting with FcγRs. However, it was subsequently demonstrated (results not shown) that the ability of the aglycosyl γ1 monoclonal antibody to mediate the destruction of mouse L cell targets (a mouse cell line which expresses the human FcγRI) was dependent on the expression of a transfected human FcγRI gene, thus confirming the FcγR binding activity of this monoclonal antibody. We conclude that the ECR assay is a particularly sensitive method of detecting Fc-FcR interactions.

The ECR results indicate that the hierarchy of binding of the IgG chimaeric antibodies is γ2<γ3<Agγ1<γ4<γ1. If the assumption is made that the mitogenic activity of an antibody is predicted by its Fc receptor binding ability, then one would expect the above hierarchy to be displayed in the T cell proliferation assays. However, this was not the case; the order of activities in T cell proliferation experiments (1 to 3) was Agγ1<γ2<γ4<γ3<γ1. This demonstrates that the mitogenicity of an antibody cannot be predicted in a straightforward fashion from the results of assays which measure Fc—Fc receptor interactions. This view is supported by the behaviour of the epsilon chimaeric antibody which performed poorly in the ECR assay and yet consistently had the highest mitogenic activity. This suggests that antibodies can activate T cells by binding to something other than Fcγ receptors (as displayed on U937 cells) on accessory cells, i.e. an inability to bind to Fcγ receptors is no guarantee that an antibody will not be mitogenic.

What is claimed is:

1. An aglycosylated IgG antibody which specifically binds CD3, having a heavy chain with three CDRs comprising the amino acid sequences (a) Ser-Phe-Pro-Met-Ala (SEQ ID NO:1), (b) Thr-Ile-Ser-Thr-Ser-Gly-Gly-Arg-Thr-Tyr-Tyr-Arg-Asp-Ser-Val-Lys-Gly (SEQ ID NO:2), (c) Phe-Arg-Gln-Tyr-Ser-Gly-Gly-Phe-Asp-Tyr (SEQ ID NO:3), or an antigen binding fragment thereof, and a light chain with three CDRs comprising the amino acid sequences:

(d) Thr-Leu-Ser-Ser-Gly-Asn-Ile-Glu-Asn-Asn-Tyr-Val-His (SEQ ID NO:4), (e) Asp-Asp-Asp-Lys-Arg-Pro-Asp (SEQ ID NO:5), (f) His-Ser-Tyr-Val-Ser-Ser-Phe-Asn-Val (SEQ ID NO:6), or an antigen binding fragment thereof, the heavy chain CDRs being arranged in the order (a), (b), (c) in the leader to constant domain direction and the light chain CDRs being arranged in the order (d), (e), (f) in the leader to constant domain direction.

2. An aglycosylated antibody according to claim 1, which specifically binds human CD3.

3. An aglycosylated antibody according to claim 1, in which the variable domain framework regions are of or are derived from those of rat or mouse origin.

4. An aglycosylated antibody according to claim 1, in which the CDRs are of different origin than the variable framework region.

5. An aglycosylated antibody according to claim 1, in which the variable domain framework regions are of or are derived from those of human origin.

6. An aglycosylated antibody according to claim 1 having a heavy chain variable domain which comprises Glu-Valn-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-Ser-Ser-Phe-Pro-Met-Ala-Trp-Val-Arg-Gln-Ala-Pro-Gly-Lys-Gly-Leu-Glu-Trp-Val-Ser-Thr-Ile-Ser-Thr-Ser-Gly-Gly-Arg-Thr-Tyr-Tyr-Arg-Asp-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-Lys-Phe-Arg-Gln-Tyr-Ser-Gly-Gly-Phe-Asp-Tyr-Trp-Gly-Gln-Gly-Thr-Leu-Val-Thr-Val-Ser-Ser (SEQ ID NO:11).

7. An aglycosylated antibody according to claim 1 having a light chain variable domain which comprises Asp-Phe-Met-Leu-Thr-Gln-Pro-His-Ser-Val-Ser-Glu-Ser-Pro-Gly-Lys-Thr-Val-Ile-Ile-Ser-Cys-Thr-Leu-Ser-Ser-Gly-Asn-Ile-Glu-Asn-Asn-Tyr-Val-His-Trp-Tyr-Gln-Gln-Arg-Pro-Gly-Arg-Ala-Pro-Thr-Thr-Val-Ile-Phe-Asp-Asp-Asp-Lys-Arg-Pro-Asp-Gly-Val-Pro-Asp-Arg-Phe-Ser-Gly-Ser-Ile-Asp-Arg-Ser-Ser-Asn-Ser-Ala-Ser-Leu-Thr-Ile-Ser-Gly-Leu-Gln-Thr-Glu-Asp-Glu-Ala-Asp-Tyr-Tyr-Cys-His-Ser-Tyr-Val-Ser-Ser-Phe-Asn-Val-Phe-Gly-Gly-Gly-Thr-Lys-Leu-Thr-Val-Leu (SEQ ID NO:16).

8. An aglycosylated antibody according to claim 1, in which the constant domains are of or are derived from those of rat or mouse origin.

9. An aglycosylated antibody according to claim 1, in which the CDRs are of different origin than the constant region.

10. An aglycosylated antibody according to claim 1, in which the constant domains are of or are derived from those of human origin.

11. An aglycosylated antibody according to claim 1, in which the constant region is of an IgG isotype.

12. An aglycosylated antibody according to claim 10, in which the constant region is of an IgG1 isotype.

13. An aglycosylated antibody according to claim 10, in which asparagine residue at position 297 of each constant region heavy chain is replaced by an alternative amino acid residue.

14. An aglycosylated antibody according to claim 13, in which the asparagine residue is replaced by an alanine residue.

15. An aglycosylated antibody according to claim 1, in which only one of the arms thereof has an affinity for CD3.

16. An aglycosylated antibody according to claim 1 which is monovalent.

17. An aglycosylated antibody according to claim 16, in which one half of the antibody consists of a complete heavy chain and light chain and the other half consists of a similar but truncated heavy chain lacking the binding site for the light chain.

18. A composition comprising an aglycosylated antibody as claimed in claim 1 together with a pharmaceutically acceptable diluent or carrier.

19. A method of immunosuppressing graft rejection, comprising administering to a patient in need thereof an immunosuppressive effective amount of an aglycosylated antibody as claimed in claim 1.

20. An aglycosylated antibody according to claim 6 having a light chain variable domain which comprises Ase-Phe-Met-Leu-Thr-Gln-Pro-His-Ser-Val-Ser-Glu-Ser-Pro-Gly-Lys-Thr-Val-Ile-Ile-Ser-Cys-Thr-Leu-Ser-Ser-Gly-Asn-Ile-Glu-Asn-Asn-Tyr-Val-His-Trp-Tyr-Gln-Gln-Arg-Pro-Gly-Arg-Ala-Pro-Thr-Thr-Val-Ile-Phe-Asp-Asp-Asp-Lys-Arg-Pro-Asp-Gly-Val-Pro-Asp-Arg-Phe-Ser-Gly-Ser-Ile-Asp-Arg-Ser-Ser-Asn-Ser-Ala-Ser-Leu-Thr-Ile-Ser-Gly-Leu-Gln-Thr-Glu-Asp-Glu-Ala-Asp-Tyr-Tyr-Cys-His-Ser-Tyr-Val-Ser-Ser-Phe-Asn-Val-Phe-Gly-Gly-Gly-Thr-Lys-Leu-Thr-Val-Leu (SEQ ID NO.16).

* * * * *

SEQUENCE LISTING

```
<160> NUMBER OF SEQ ID NOS: 26

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: artificial
      peptide

<400> SEQUENCE: 1

Ser Phe Pro Met Ala
 1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:  artificial
      peptide

<400> SEQUENCE: 2

Thr Ile Ser Thr Ser Gly Gly Arg Thr Tyr Tyr Arg Asp Ser Val Lys Gly
 1               5                  10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: artificial
      peptide

<400> SEQUENCE: 3

Phe Arg Gln Tyr Ser Gly Gly Phe Asp Tyr
 1               5                  10

<210> SEQ ID NO 4
<211> LENGTH: 13
<212> TYPE: PRT
<213> ORGANISM: Artificial Sequence
<220> FEATURE:
```

```
<223> OTHER INFORMATION: Description of Artificial Sequence:  artificial
      peptide

<400> SEQUENCE: 4

Thr Leu Ser Ser Gly Asn Ile Glu Asn Asn Tyr Val His
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:  artificial
      peptide

<400> SEQUENCE: 5

Asp Asp Asp Lys Arg Pro Asp
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:  artificial
      peptide

<400> SEQUENCE: 6

His Ser Tyr Val Ser Ser Phe Asn Val
 1               5

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence:   artificial
      peptide

<400> SEQUENCE: 7

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser
             20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:  artificial
      peptide

<400> SEQUENCE: 8

Trp Val Arg Gln Ala Pro Gly Lys Gly Leu Glu Trp Val Ser
 1               5                  10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence:  artificial
      peptide

<400> SEQUENCE: 9

Arg Phe Thr Ile Ser Arg Asp Asn Ser Lys Asn Thr Leu Tyr Leu Gln
```

```
              1               5              10              15
Met Asn Ser Leu Arg Ala Glu Asp Thr Ala Val Tyr Tyr Cys Ala Lys
                     20              25              30
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: artificial
      peptide

<400> SEQUENCE: 10

```
Trp Gly Gln Gly Thr Leu Val Thr Val Ser Ser
 1               5                  10
```

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: artificial
      peptide

<400> SEQUENCE: 11

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
             20                  25                  30

Pro Met Ala Trp Val Arg Gln Ala Pro Gly Lys Gly Leu Glu Trp Val
         35                  40                  45

Ser Thr Ile Ser Thr Ser Gly Gly Arg Thr Tyr Tyr Arg Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115
```

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: artificial
      peptide

<400> SEQUENCE: 12

```
Asp Phe Met Leu Thr Gln Pro His Ser Val Ser Glu Ser Pro Gly Lys
 1               5                  10                  15

Thr Val Ile Ile Ser Cys
             20
```

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: artificial
      peptide

<400> SEQUENCE: 13

Trp Tyr Gln Gln Arg Pro Gly Arg Ala Pro Thr Thr Val Ile Phe
 1               5                  10                  15

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: artificial
      peptide

<400> SEQUENCE: 14

Gly Val Pro Asp Arg Phe Ser Gly Ser Ile Asp Arg Ser Ser Asn Ser
 1               5                  10                  15

Ala Ser Leu Thr Ile Ser Gly Leu Gln Thr Glu Asp Glu Ala Asp Tyr
            20                  25                  30

Tyr Cys

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: artificial
      peptide

<400> SEQUENCE: 15

Phe Gly Gly Gly Thr Lys Leu Thr Val Leu
 1               5                  10

<210> SEQ ID NO 16
<211> LENGTH: 110
<212> TYPE: PRT
<213> ORGANISM: Artificial Sequence
<220> FEATURE:
<223> OTHER INFORMATION: Description of Artificial Sequence: artificial
      peptide

<400> SEQUENCE: 16

Asp Phe Met Leu Thr Gln Pro His Ser Val Ser Glu Ser Pro Gly Lys
 1               5                  10                  15

Thr Val Ile Ile Ser Cys Thr Leu Ser Ser Gly Asn Ile Glu Asn Asn
            20                  25                  30

Tyr Val His Trp Tyr Gln Gln Arg Pro Gly Arg Ala Pro Thr Thr Val
        35                  40                  45

Ile Phe Asp Asp Asp Lys Arg Pro Asp Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Gln Thr Glu Asp Glu Ala Asp Tyr Tyr Cys His Ser Tyr Val Ser
                85                  90                  95

Ser Phe Asn Val Phe Gly Gly Gly Thr Lys Leu Thr Val Leu
            100                 105                 110

<210> SEQ ID NO 17
<211> LENGTH: 15
<212> TYPE: DNA
<213> ORGANISM: Unknown Organism
<220> FEATURE:
<223> OTHER INFORMATION: Description of Unknown Organism: unknown

<400> SEQUENCE: 17
agctttccaa tggcc                                                         15

<210> SEQ ID NO 18
<211> LENGTH: 51
<212> TYPE: DNA
<213> ORGANISM: Unknown Organism
<220> FEATURE:
<223> OTHER INFORMATION: Description of Unknown Organism: unknown

<400> SEQUENCE: 18
accattagta ctagtggtgg tagaacttac tatcgagact ccgtgaaggg c                 51

<210> SEQ ID NO 19
<211> LENGTH: 30
<212> TYPE: DNA
<213> ORGANISM: Unknown Organism
<220> FEATURE:
<223> OTHER INFORMATION: Description of Unknown Organism: unknown

<400> SEQUENCE: 19
tttcggcagt acagtggtgg ctttgattac                                         30

<210> SEQ ID NO 20
<211> LENGTH: 39
<212> TYPE: DNA
<213> ORGANISM: Unknown Organism
<220> FEATURE:
<223> OTHER INFORMATION: Description of Unknown Organism: unknown

<400> SEQUENCE: 20
acactcagct ctggtaacat agaaaacaac tatgtgcac                               39

<210> SEQ ID NO 21
<211> LENGTH: 21
<212> TYPE: DNA
<213> ORGANISM: Unknown Organism
<220> FEATURE:
<223> OTHER INFORMATION: Description of Unknown Organism: unknown

<400> SEQUENCE: 21
gatgatgata agagaccgga t                                                  21

<210> SEQ ID NO 22
<211> LENGTH: 27
<212> TYPE: DNA
<213> ORGANISM: Unknown Organism
<220> FEATURE:
<223> OTHER INFORMATION: Description of Unknown Organism: unknown

<400> SEQUENCE: 22
cattcttatg ttagtagttt taatgtt                                            27

<210> SEQ ID NO 23
<211> LENGTH: 357
<212> TYPE: DNA
<213> ORGANISM: Unknown Organism
<220> FEATURE:
<223> OTHER INFORMATION: Description of Unknown Organism: unknown

<400> SEQUENCE: 23
gaggtccaac tgctggagtc tgggggcggt ttagtgcagc ctggagggtc cctgagactc        60
tcctgtgcag cctcaggatt cactttcagt agctttccaa tggcctgggt ccgccaggct       120
ccagggaagg gtctggagtg ggtctcaacc attagtacta gtggtggtag aacttactat       180

```
cgagactccg tgaagggccg attcactatc tccagagata atagcaaaaa tacctatac      240 ctgcaaatga atagtctgag ggctgaggac acggccgtct attactgtgc aaaatttcgg     300
cagtacagtg gtggctttga ttactggggc caagggaccc tggtcaccgt ctcctca        357

<210> SEQ ID NO 24
<211> LENGTH: 330
<212> TYPE: DNA
<213> ORGANISM: Unknown Organism
<220> FEATURE:
<223> OTHER INFORMATION: Description of Unknown Organism: unknown

<400> SEQUENCE: 24
gacttcatgc tgactcagcc ccactctgtg tctgagtctc cggaaagac agtcattatt      60 tcttgcacac tcagctctgg taacatagaa aacaactatg tgcactggta ccagcaaagg    120
ccgggaagag ctcccaccac tgtgattttc gatgatgata agagaccgga tggtgtccct    180
gacaggttct ctggctccat tgacaggtct tccaactcag cctccctgac aatcagtggt    240
ctgcaaactg aagatgaagc tgactactac tgtcattctt atgttagtag ttttaatgtt    300
ttcggcggtg gaacaaagct cactgtcctt                                     330

<210> SEQ ID NO 25
<211> LENGTH: 130
<212> TYPE: PRT
<213> ORGANISM: Artificial Sequence
<220> FEATURE:
<223> OTHER INFORMATION: Description of Artificial Sequence: artificial
      peptide

<400> SEQUENCE: 25

Asp Phe Met Leu Thr Gln Pro His Ser Val Ser Glu Ser Pro Gly Lys
  1               5                  10                  15

Thr Val Ile Ile Ser Cys Thr Leu Ser Ser Gly Asn Ile Glu Asn Asn
             20                  25                  30

Tyr Val His Trp Tyr Gln Gln Arg Pro Gly Arg Ala Pro Thr Thr Val
         35                  40                  45

Ile Phe Asp Asp Asp Lys Arg Pro Asp Gly Val Pro Asp Arg Phe Ser
     50                  55                  60

Gly Ser Ile Asp Arg Ser Ser Asn Ser Ala Ser Leu Thr Ile Ser Gly
 65                  70                  75                  80

Leu Gln Thr Glu Asp Glu Ala Asp Tyr Tyr Cys His Ser Tyr Val Ser
                 85                  90                  95

Ser Phe Asn Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln
    130

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: artificial
      peptide

<400> SEQUENCE: 26
```

-continued

```
Phe Gly Gly Gly Thr Lys Leu Thr Val Leu Gly Gln Pro Lys Ala Ala
 1               5                   10                  15

Pro Ser Val Thr Leu Phe Pro Pro Ser Ser Glu Glu Leu Gln
                20              25              30
```